Figure 1:
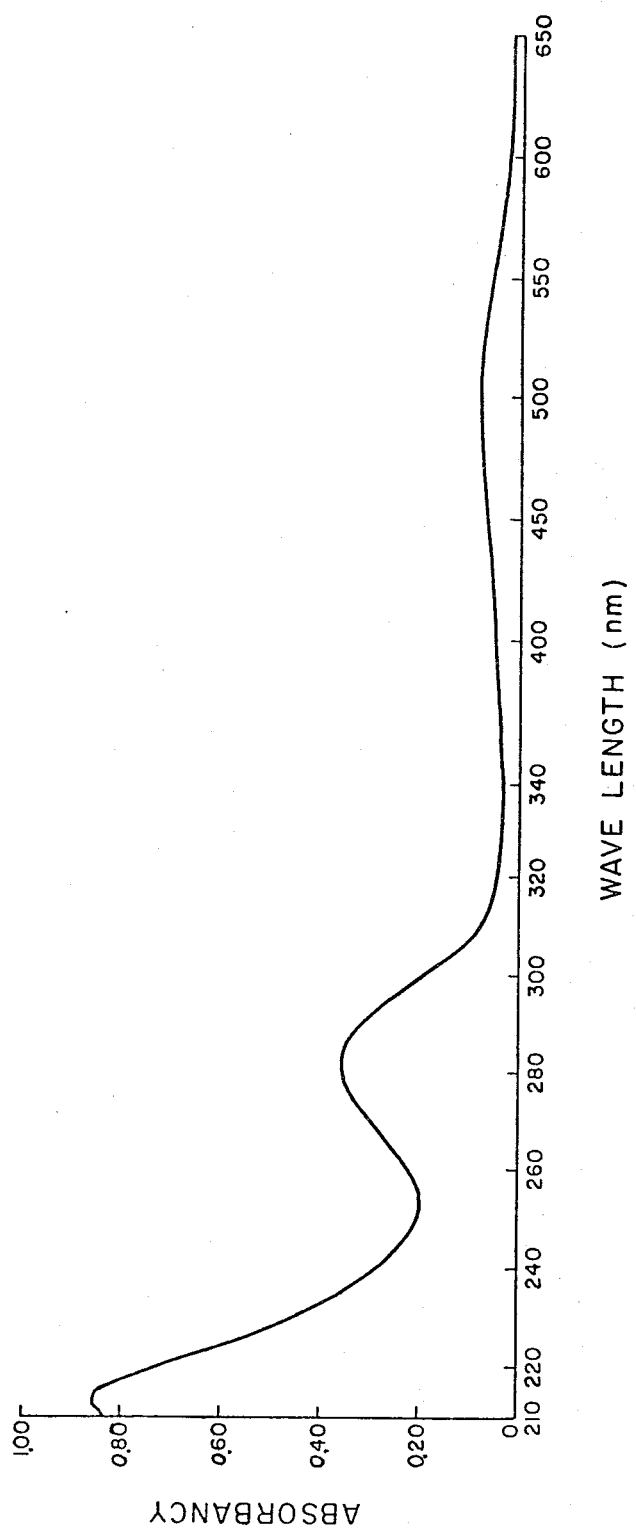

United States Patent [19]

Higashide et al.

[11] 4,292,309

[45] Sep. 29, 1981

[54] ANTIBIOTICS C-14482 $B_1$, $B_2$ AND $B_3$

[75] Inventors: Eiji Higashide, Takarazuka; Seiichi Tanida, Nagaokakyo; Masayuki Muroi, Suita; Mitsuko Asai, Takatsuki, all of Japan

[73] Assignee: Takeda Chemical Industries, Ltd., Osaka, Japan

[21] Appl. No.: 113,131

[22] Filed: Jan. 17, 1980

[30] Foreign Application Priority Data

Feb. 2, 1979 [JP] Japan .................................. 54-11561

[51] Int. Cl.$^3$ ......................... A61K 35/74; C12P 1/04; C12N 1/20
[52] U.S. Cl. ................................... 424/119; 435/170; 435/253; 424/120
[58] Field of Search ................ 435/170, 253; 424/119, 424/120

[56] References Cited

FOREIGN PATENT DOCUMENTS 2001954 2/1979 United Kingdom ................ 435/170

*Primary Examiner*—Lionel M. Shapiro
*Attorney, Agent, or Firm*—Wenderoth, Lind & Ponack

[57] ABSTRACT

Novel antibiotics C-14482 $B_1$, $B_2$ and $B_3$ are produced by cultivating a microorganism belonging to the genus Nocardia and capable of producing Antibiotics C-14482 $B_1$, $B_2$ and/or $B_3$ in a culture medium, whereby Antibiotics C-14482 $B_1$, $B_2$ and/or $B_3$ are elaborated and accumulated in the cultured broth and are recovered.

Antibiotics C-14482 $B_1$, $B_2$ and $B_3$ are useful as a germicide or disinfectant, respectively.

5 Claims, 4 Drawing Figures

ANTIBIOTICS C-14482 $B_1$, $B_2$ AND $B_3$

The present invention relates to Antibiotics C-14482 $B_1$, $B_2$ and $B_3$ which are novel antibiotics, respectively, and a method for producing said antibiotics.

The present inventors have collected samples from the natural kingdom including a great variety of soil and plant samples and have undertaken screenings of the microorganisms and artificial mutants thereof isolated from such samples for the antibiotics which they might produce. This exploration and investigation resulted in the discoveries that a certain microorganism is able to produce novel antibiotics, that such microorganism belongs to the genus Nocardia and that cultivating said microorganism in a suitable nutrient medium under controlled fermentation conditions results in the accumulation of said antibiotics in the culture broth. These findings were followed by further research, which has culminated in this invention.

The present invention is, therefore, concerned with:

(1) Antibiotics C-14482 $B_1$, $B_2$, $B_3$ and their salts, (2) a method for producing Antibiotics C-14482 $B_1$, $B_2$ and/or $B_3$ characterized by cultivating a microorganism which belongs to the genus Nocardia and is capable of producing Antibiotics C-14482 $B_1$, $B_2$ and/or $B_3$ (hereinafter sometimes referred to briefly as "Antibiotic C-14482 producing microorganism" or "C-14482 B producing microorganism") in a culture medium to have Antibiotics C-14482 $B_1$, $B_2$ and/or $B_3$ (hereinafter sometimes referred to briefly as "Antibiotic C-14482 B" or "C-14482 B") produced and accumulated in the culture broth and harvesting the antibiotics, and (3) a microorganism belonging to the species of Nocardia sp. No. C-14482 which exhibits the resistance to lincomycin, penicillin G and streptomycin and is capable of producing Antibiotics C-14482 $B_1$, $B_2$ and/or $B_3$.

In this specification, Antibiotics C-14482 $B_1$, $B_2$ and $B_3$ are sometimes referred to briefly as "C-14482 $B_1$", "C-14482 $B_2$" and "C-14482 $B_3$", respectively.

Examples of the microorganism which is usable in the present invention include the Nocardia sp. No. C-14482 IFO 13725 strain (hereinafter sometimes referred to briefly as "IFO 13725 strain"), an actinomycete which we isolated in the course of our search for antibiotic-producing microorganisms, and the Nocardia sp. No. C-14482 IFO 13887 strain (hereinafter sometimes referred to briefly as "IFO 13887 strain"), a mutant strain obtained from the above parent strain through the conventional mutation means. They are new species of microorganisms belonging to a new type of the genus Nocardia as will be seen from the following description.

Microbiological characteristics of the IFO 13725 strain are investigated in accordance with the method of Schirling and Gottlieb [International Journal of Systematic Bacteriology, 16, 313-340, (1966)]. The observation results obtained with cultures of the microorganisms at 28° C. for 21 days are as follows:

(1) Morphological characteristics

The vegetative mycelium is colorless to pale yellow or orange yellow, and develops well with branching both on agar and in liquid media. The vegetative mycelium measures 0.5 to 1.2 μm in diameter for the most part and, in last phases of the cultivation, divides itself into fragments resembling rod bacteria, elongated rod bacteria or branched hyphae. This strain grows well on various media and, while the aerial mycelia develop well on the vegetative mycelium, they appear in many cases as if they had grown on a large number of coremia-like bodies (50 to 180 μm×400 to 1500 μm). Many of the aerial hyphae are flexuous or straight but some appear to be loosely spiral on but rare occasions. Microscopic examination of aged cultures reveals that in few cases do the spores occur in chains, there being few of what are called conidia or spores. When examined under a microscope, cells taken from the surface of such a culture revealed the presence of many elongated ellipsoidal (0.5 to 1.2 μm×4.8 to 6.8 μm) and ellipsoidal (0.8 to 1.2 μm×1.5 to 4 μm) cells which looked like fragmented cells or arthrospores, the surfaces of which were smooth as examined by electron microscope. The aerial mycelium is generally sparse and, although fair growth is noted on many media over 3 to 7 days of incubation, it sometimes disappears as cultivation is carried out for more than 10 days.

When cultivated in liquid media, the microorganism shows mobility in a growing phase when the mycelia show the polymorphism, i.e. the forms of rod, branched cells thereof or elongated rod, either as they are independent, in chains or branched. Electron microscopic examination shows a large number of elongated flagella around the cells.

(2) The constituents of cells

The strain was shaken-cultured in modified ISP No. 1 medium at 28° C. for 66 to 90 hours and in the well grown stationary phase, the cells were collected and rinsed. By the method of B. Becker et al. [Applied Microbiology, 12,421(1964)] and the method of M. P. Lechevalier [Journal of Laboratory and Clinical Medicine, 71, 934(1968)], the above cells were examined for diaminopimelic acid and sugar composition. The former was found to be the mesoform and, as to the latter, spots corresponding to galactose and arabinose, respectively, were observed. In accordance with the method of B. Becker et al. [Applied Microbiology, 17, 236 (1965)], cell walls were also collected and analyzed for diaminopimelic acid, sugar and amino acids. Regarding diaminopimelic acid, its meso-form was detected. However, while a large amount of galactose was in evidence as the constituent sugar, there was no evidence of arabinose. As to amino acids, glutamic acid and alanine were clearly detected, although lysine and glycine could be found only in traces.

(3) Cultural characteristics

The strain gives comparatively good growth invariably on various media and the color of the vegetative mycelium is colorless to pale yellow in the early phases of incubation but is pale yellowish brown to yellow brown hues in later stages. The organism does not produce soluble pigments in most media but produces lightly brown, soluble pigments in a few media. The aerial mycelium is powdery, generally grows to a moderate extent, and represents white to yellow or pale yellowish brown color. The aerial mycelium disappears on many media on prolonged culture (approximately two weeks or more), with the surface of vegetative mycelium beginning to become glossy. The cultural features of this particular strain on various media are summarized in Table 1.

TABLE 1: Cultural characteristics of strain IFO 13725 on various media (A) Sucrose nitrate agar:

Growth (G): Poor, thin, colorless
Aerial mycelium (AM): Sparse, white
Soluble pigment (SP): None
(B) Glucose nitrate agar:
  G: Poor, thin, colorless
  AM: Very sparse, white
  SP: None
(C) Glycerol nitrate agar:
  G: Moderate, colorless to Lt Lemon Yellow or Colonial Yellow Maize (3ea or 2ga)* or Brite Melon Yellow (3ia)*; coremia-like bodies formed.
  AM: Very sparse, white to Lt Melon Yellow (3ea)*
  SP: None
(D) Glucose asparagine agar:
  G: Moderate, colorless to Melon Yellow (3ga)*
  AM: Sparse, Lt Melon Yellow (3ea)*
  SP: None
(E) Glycerol asparagine agar:
  G: Moderate, colorless to Melon Yellow (3ga)*
  AM: Moderate, white to Lt Wheat (2ea)*
  SP: None
(F) Nutrient agar:
  G: Moderate, colorless to Lt Ivory (2ca)* or Melon Yellow (3ga)*
  AM: None
  SP: None
(G) Calcium malate agar:
  G: Moderate, colorless to Melon Yellow (3ga)* or Brite Marigold (3pa)*; coremia-like bodies formed
  AM: Sparse, white
  SP: None
(H) Yeast extract-malt extract agar:
  G: Luxuriant, colorless to Melon Yellow (3ga)* or Brite Maize (31a)*; coremia-like bodies formed
  AM: Moderate, white to Pearl Pink (3ca)* or Lt Melon Yellow (3ea)*
  SP: Pale yellowish brown
(I) Oatmeal agar:
  G: Moderate, colorless to Melon Yellow (3ga)* or Lt Ivory (2ca)*
  AM: Moderate, white to Lt Melon Yellow (3ea)* or Pearl Pink (3ca)*
  SP: None or pale yellowish brown
(J) Starch agar:
  G: Moderate, colorless to Melon Yellow or Colonial Yellow Maize (3ga or 2ga)*
  AM: Sparse, white to Lt Melon Yellow (3ea)*
  SP: None
(K) Peptone-yeast extract iron agar:
  G: Moderate, colorless to Beige Brown (3ig)* or Brite Maize (31a)*
  AM: None or sparse, white
  SP: Pale yellowish brown
(L) Tyrosine agar:
  G: Moderate, colorless to Beige Brown (3ig)* or Brite Maize (31a)*; coremia-like bodies formed
  AM: Sparse, Pearl Pink (3ca)* or Brite Maize (31a)*
  SP: Light yellowish brown (a tinge of purple)

Remarks (*); The color codes according to Color Harmony Manual, 4th ed. (Container Corporation of America, 1958).

(4) Physiological characteristics

The physiological characteristics of the strain are shown in Table 2. Temperature range for growth: 12° to 38° C. The temperature range for which the aerial mycelia grow on agar media (ISP No.2) is 20° to 35° C.

TABLE 2

The physiological characteristics of strain IFO 13275.

| | |
|---|---|
| Temperature range for the growth: | 12° to 38° C. |
| Temperature range for the growth of the aerial mycelia: | 20° to 35° C. |
| Liquefaction of gelatin: | Very weak |
| Hydrolysis of starch: | Positive |
| Reduction of nitrates: | Positive |
| Peptonization of milk: | Positive |
| Coagulation of milk: | Negative |
| Decomposition of casein: | Positive |
| Production of melanoid pigments: | |
| (Peptone yeast extract iron agar): | Negative |
| (tyrosine agar): | Negative |
| Decomposition of tyrosine: | Positive |
| Decomposition of xanthine: | Negative |
| Decomposition of hypoxanthine: | Negative |
| Tolerance to lysozyme: | Positive |
| Tolerance to sodium chloride: | 2% |

(5) Utilization of various carbon sources

The utilization of various carbon sources was investigated using a medium described in the method of Pridham and Gottlieb [Journal of Bacteriology, 56, 107(1948)] and a basal medium of the same composition supplemented with 0.1% of yeast extract (Difco. Co.). The results are shown in Table 3.

TABLE 3

The utilization of carbon sources by strain IFO 13725.

| Source of carbon | Growth | |
|---|---|---|
| D-Xylose | + | + +* |
| L-Arabinose | − | + |
| D-Glucose | + + | + + |
| D-Galactose | + + | + + |
| D-Fructose | + + + | + + + |
| L-Rhamnose | + + | + |
| D-Mannose | + + | + + + |
| Sucrose | + + | + + |
| Maltose | + | + + |
| Trehalose | + + | + + |
| Raffinose | ± | − |
| Melibiose | ± | ± |
| i-Inositol | − | ± |
| D-Sorbitol | − | ± |
| D-Mannitol | + + | + + |
| Glycerol | + + | + + + |
| Soluble starch | + | + + |
| Control | − | − |

Remarks:
*; Basal medium added with 0.1% of yeast extract
+ + +; Luxuriant growth
+ +; Good growth
+; Growth
±; Poor growth
−; No growth (6) Other characteristics The cells were harvested by the procedure as described under the item, "(2) The constituents of cells", and were treated to prepare DNA in accordance with the procedure of J. Murmar et al. [Journal of Molecular Biology, 3, 208 (1969)]. The G-C (guanine-cytosine) content of the DNA was found to be about 71 mole %.

Gram-staining of the vegetative mycelium of this strain was positive.

The above-mentioned characteristics of strain IFO 13725 were compared with the descriptions in S. A. Waksman, "The Actinomycetes Vol. 2" (The Williams and Wilkins Co., 1961); R. E. Buchanan and N. E. Gibbons, "Bergy's Manual of Determinative Bacteriology," 8th ed., 1974; and other literature references.

The above observations that (1) the strain in later phases of incubation is fragmented into the forms of rod or elongated rod, or branched cells thereof, (2) it gives few well-defined conidia or spores, (3) the surfaces of its colonies on agar are leathery and, in many cases, are glistening like bacterial colonies, and (4) the G-C content of the mycelium is about 71 mole %, coupled with other characteristics, suggest that the strain might belong to Group III of the genus Nocardia. However, in view of our inability to find out any known strain of microorganism which shared all of the above cultural characteristics on media, physiological characteristics, cell mobility, cell wall composition, etc. with our present strain, we identified this strain as a novel species.

The strain IFO 13725 has been deposited in the following culture collections with the accession numbers indicated as follows: Institute for Fermentation, Osaka, Japan, IFO 13725; Fermentation Research Institute, Agency of Industrial Science and Technology, Japan, FERM-P No.4130; The American Type Culture Collection (U.S.A.), ATCC 31309.

Generally, microorganisms of the genus Nocardia are liable to undergo variations and mutations, whether spontaneously or under the influence of a mutagen. For example, the many variants of the strain which are obtainable by irradiation with X-ray, gamma ray, ultraviolet radiation, etc., by culture on media containing various chemicals, or by any other mutagenesis, as well as the mutants spontaneously obtained from the strain, should not be considered to represent any other distinct species, when compared with the above-mentioned microbiological properties or those to be shown below, but any of such variants and mutants, if capable of elaborating C-14482 B, may be invariably utilized for the purpose of this invention. By way of example, subjecting the C-14482 B producing strain to mutagenesis yields variants which product light yellow to light yellowish brown or brown soluble pigments, variants which give colorless vegetative mycelia, variants which give reddish brown to orange red vegetative mycelia, variants which give yellowish green vegetative mycelia or soluble pigments, variants which give abundant aerial mycelia which are white in color, or variants whose mycelia are ready to be fragmented.

For example, a conventional mutagenesis effected with the strain IFO 13725 as the parent strain yields the strain IFO 13887, a variant capable of producing advantageously Antibiotic C-14482 B. This strain has the capability to produce C-14482 B in increased quantities as compared with the parent strain thereof, and is similar in taxonomical characteristics to the parent strain, except the physiological properties shown in Table 4.

TABLE 4

| Susceptibility toward antibiotic (minimum inhibition concentration, μg/ml) | |
|---|---|
| | Strain IFO 13725 | Strain IFO 13887 |
| Lincomycin | 5 | 20 |
| Penicillin G | 10 | 50 |
| Streptomycin | 1 | 5 |
| Tetracycline | 0.5 | 1 |
| Chloramphenicol | 10 | 5 |
| Rifampicin | <0.1 | <0.1 |

The strain IFO 13887 has been deposited in the culture collections with the accession numbers indicated. Institute for Fermentation, Osaka, Japan, IFO 13887; Fermentation Research Institute, Agency of Industrial Science and Technology, Japan, FERM-P No.4779 and The American Type Culture Collection (U.S.A.), ATCC 31487.

The specific method of obtaining the strain IFO 13887 for example comprises cultivating the parent strain IFO 13725 on a plate containing yeast extract-malt extract agar (ISP-2) at 32° C. for 4 days, collecting hyphae grown to suspend them in a 0.05 M potassium phosphate buffer, filtering the suspension with a filter paper, and effecting a variation inducing treatment as described in the following: for example, the resultant filtrate is irradiated with ultraviolet radiation so that the number of viable cells may be in the range of 2%, and is immediately applied to a plate of yeast extract-malt extract agar containing 10 μg/ml of lincomycin to incubate the culture at 32° C. for 6 days. In this way, the strain IFO 13887 was able to be obtained from the resultant colonies.

The said variant strain is inoculated into a culture medium for production of antibiotics to carry out a cultivation, whereby the produced amounts of Antibiotics C-14482 $B_1$, $B_2$ and $B_3$ in the culture are found to increase as compared with the case of the parent strain.

The novel species, Nocardia sp. No. C-14482, exhibits for example the following characteristics:

(1) Gram-positive (2) The vegetative mycelium is 0.5 to 1.2 μm in diameter and develops well. It breaks partly into fragments resembling rod bacteria or elongated rod bacteria, and shows the mobility. (However, out of its variants, some fragment less and the others may fragment markedly.).

(3) Adhesion of the aerial mycelium varies with the properties of the strains. That is to say; normally, the aerial mycelium which is white to yellow adheres, whereas it hardly adheres with the variant strains.

(4) The aerial mycelium is allowed to float on a liquid medium to be permitted to stand at a suitable temperature for about 30 minutes, whereby the motile cells are observed.

(5) Meso-diaminopimelic acid and galactose are contained in the cell walls.

The medium which is useful in the cultivation of the C-14482 B producing microorganism may be either in the liquid or solid state, only if it contains nutrient sources which the microorganism can utilize, although a liquid medium is preferred for large-scale operations. Suitably formulated into the medium are carbon and nitrogen sources which the C-14482 B producing microorganism can assimilate and digest, respectively, inorganic substances, trace nutrients, etc. As examples of said carbon sources there may be mentioned glucose, lactose, sucrose, maltose, dextrin, starch, glycerol, mannitol, sorbitol, fats and oils (e.g. soybean oil, lard oil, chicken oil, etc.), n-paraffin and so forth. The nitrogen sources may for example be meat extract, yeast extract, dried yeast, soybean meal, corn steep liquor, peptone, cottonseed flour, spent molasses, urea, ammonium salts (e.g. ammonium sulfate, ammonium chloride, ammonium nitrate, ammonium acetate, etc.), and others. The medium may further contain salts of sodium, potassium, calcium, magnesium, etc., salts of iron, manganese, zinc, cobalt, nickel, etc., salts of phosphoric acid, boric acid, etc., and salts of organic acids such as acetic acid and propionic acid. Further, the medium may contain, as added, various amino acids (e.g. glutamic acid, aspartic acid, alanine, lysine, methionine, proline, etc.), peptides (e.g. dipeptides, tripeptides, etc.), vitamins (e.g. $B_1$, $B_2$, nicotinic acid, $B_{12}$, C, etc.), nucleic acids (e.g. purine, pyrimidine and derivatives thereof, etc.) and so forth. For the purpose of adjusting the pH of the medium, there may be added an inorganic or organic acid, alkalis, buffer or the like, while suitable amounts of oils and fats, surfactants, etc. may be added for the purpose of defoaming.

The cultivation may be conducted by any of the stationary, shake, submerged aerobic and other cultural methods. For big-volume production runs, submerged aerobic culture is of course preferred. While the conditions of culture depend upon the conditions and composition of the medium, type of the strains, cultural method and other factors, it is normally preferable to carry out incubation at 20° to 32° C. with an initial pH of about neutral. Particularly desirable in a temperature from 25° to 28° C. in an intermediate stage of cultivation, with an initial pH of 6.5 to 7.5. While the incubation time also depends on the same factors as mentioned above, it is advisable to continue the incubation until the titer of the desired antibiotic becomes maximal. In the case of shake culture or submerged aerobic culture in a liquid medium, the time required normally ranges from about 72 to 192 hours.

From the culture broth obtained in the above method, Antibiotic C-14482 B can be advantageously isolated and recovered by the procedures which are normally utilized in the recovery of metabolites from microbial cultures. For example, Antibiotic C-14482 B is weakly basic and fairly soluble in halogenated hydrocarbons and alcohols, and can therefore be isolated and recovered by a suitable combination of the procedures utilizing these properties.

Since Antibiotic C-14482 B occurs primarily in the filtrate of the culture broth and is more soluble in an acidic water and more stable in the acidic region, the broth is acidified with inorganic acid such as hydrochloric acid and sulfuric acid or organic acid such as oxalic acid and acetic acid and is subjected to filtration to remove the microbial cells, followed by making the resultant filtrate of the culture neutral or weakly basic to isolate and recover the antibiotic with the use of an organic solvent immiscible with water. Examples of the organic solvent which is suited for the extraction include alcohols (e.g. n-butnol, iso-butanol, etc.) and halogented hydrocarbons (e.g. chloroform, methylene chloride, etc.). In addition, esters of fatty acids (e.g. ethyl acetate, butyl acetate, etc.), ketones (e.g. methyl isobutyl ketone) and the like are fairly useful to recover Antibiotic C-14482 B, when these solvents are used for extraction while salting out with sodium chloride, ammonium sulfate, etc.

The present Antibiotic C-14482 B thus extracted in the organic solvent can then be transferred into a water phase by means of a dilute aqueous mineral acid, a dilute aqueous organic acid or an acidic buffer solution, and be thus purified.

Furthermore, Antibiotic C-14482 B as it occurs in the cells can be extracted from the cells with a freely water-miscible organic solvent, a dilute aqueous mineral acid or a mixture thereof.

In certain cases, further, the culture broth containing the cells can as such be made weakly acidic and stirred with an added, freely water-miscible organic solvent such as acetone and methanol, followed by conducting extraction and filtration to concentrate under reduced pressure; the resultant concentrate is treated in the same manner as described for the filtrate of the culture broth.

An alternative procedure for recovering Antibiotic C-14482 from the filtrate of the cultured broth comprises adsorbing the active substance with an adsorbent and eluting it with a suitable solvent. As examples of the adsorbent, there may be mentioned activated carbon, nonionic exchange porous resin. As preferred examples of the eluant, there may be mentioned aqueous alcohols (e.g. aqueous methanol, aqueous n-propanol, aqueous isobutanol, etc.), aqueous acetone or those aqueous media as previously made acidic by the addition of a dilute mineral acid or the like, although Antibiotic C-14482 B may be eluted with an organic solvent such as ethyl acetate and chloroform or its mixture with water (e.g. ethyl acetate saturated with water or water saturated with ethyl acetate).

It is also possible to isolate Antibiotic C-14482 B by, taking advantage of its weakly basic property, adsorbing it on a cation exchange material such as cation exchange resin, cation exchange cellulose and cation exchange Sephadex, and desorbing it with a variety of eluants.

To elute the active substance from the ion exchange material, use may be made of a dilute aqueous solution of mineral acid such as dilute hydrochloric acid, an aqueous solution of a salt such as sodium chloride, ammonium formate and ammonium acetate, a basic aqueous solution such as dilute aqueous ammonia and dilute aqueous pyridine, and their mixture with water-soluble organic solvents such as methanol and acetone.

By a suitable combination of the above-mentioned purification procedures according to the contents of the active components and impurities in, and the composition of, the cultured broth, the desired component substance with a high degree of purity can be obtained. To obtain a purified product with a higher degree or purity, such adsorbent material as silica gel, alumina or dextran gel in non-aqueous solvents such as Sephadex LH-20 (Pharmacia Co., Sweden) may be employed.

As examples of the developing solvent, there may be mentioned, in the case of silica gel used as the adsorbent material, the solvents which are normally employed for the separation of organic compounds; for example, halogenated solvents (chloroform, methylene chloride, etc.), alcohols (e.g. methanol, ethanol, etc.), and, among others, mixtures thereof such as a mixture of chloroform and methanol, and mixtures of esters (e.g. ethyl acetate) and alcohols.

For the purpose of further purification, methods utilizing the differences in the distribution coefficient methods utilizing certain adsorbents, etc. may be mentioned.

Namely, often in a culture of the strain IFO 13725, one of the C-14482 B producing microorganisms, there are simultaneously produced several active substances having the similar property; or, C-14482 $A_1$ (Japanese Patent Laying-open No. 27501/1979), C-14482 $B_1$, $B_2$ and $B_3$ may be mentioned. To separate them from each other, the following procedures for separation and purification can be utilized.

Examples of the methods utilizing the difference in the distribution coefficient may include the distribution method which utilizes differences in the distribution coefficients of various components between two different solvents forming two immiscible phases, the counter-current distribution method and the partition chromatography using cellulose powder, etc. as the support material.

When partitioned between chloroform and water at pH 8.0, for example, C-14482 $B_1$ and $B_2$ show the larger solubility in the chloroform layer but the decreased distribution coefficient as compared with C-14482 $A_1$. When partitioned between chloroform and water at pH 5, in contrast to this, C-14482 $B_1$ and $B_2$ migrate into the water layer, whereas C-14482 $A_1$ remains to a fairly great extent in the chloroform layer.

In the case of the adsorption method in which silica gel is for example used as the adsorbent, the mixture of C-14482 $B_1$, $B_2$ and $B_3$ is chromatographed on a column or thin layer of silica gel, followed by developing for example with a mixed solvent of chloroform and methanol, resulting in separation into C-14482 $A_1$ and C-14482 $B_1$, $B_2$ and $B_3$.

In addition, C-14482 $A_1$ and C-14482 $B_1$, $B_2$ and $B_3$, when chromatographed on a column of Amberlite XAD-2 (Rohm & Haas Co., U.S.A.), are found to present the difference in adsorption property in the acidic conditions, and can be separated from each other by taking advantage of this.

C-14482 $B_1$, $B_2$ and $B_3$, when being chromatographed on thin layer silica gel with the use of a mixed solvent system of ethyl acetate and methanol, etc., are separated from each other, yielding the purified products of $B_1$, $B_2$ and $B_3$. In case C-14482 $B_1$, particularly, is present as the principal component in fairly large quantities in the culture, the silica gel thin layer chromatography, the procedure for separating C-14482 $B_1$, $B_2$ and $B_3$ from each other, column chromatography with silica gel or non-ionic exchange resin, the procedure for separating from C-14482 $A_1$, and other steps may be omitted, and, instead, a crude product is merely recrystallized from chloroform or acetone-hexane, etc., resulting in isolation of C-14482 $B_1$.

Out of Antibiotic C-14482 $B_1$, $B_2$ and $B_3$ thus purified and separated, C-14482 $B_1$ is obtained as reddish brown crystals from acetone-hexane or chloroform, whereby the crystals from chloroform normally contain about 1 mole of chloroform as the solvent of crystallization; C-14482 $B_2$ and $B_3$ represent the trace components and are obtained normally as reddish brown, amorphous powder but not as crystals.

C-14482 $B_2$ is liable to change into C-14482 $B_1$, etc., during purification procedure, and is still difficult to be isolated as crystals even through the purification procedure carefully conducted at low temperature. From the fact that it is ready to change into $B_1$ in a solution, etc., the substance is estimated to be a compound similar to $B_1$, though the chemical structure relationship between them is not clear.

Nevertheless, the distinct difference of C-14482 $B_2$ from C-14482 $B_1$ is detected on the thin layer chromatograms with silica gel. That is to say: with the solvent system (1), the Rf value is 0.37 for C-14482 $B_1$ but 0.43 for C-14482 $B_2$; in the solvent system (2), the Rf value is 0.31 for C-14482 $B_1$, whereas it is 0.23 for C-14482 $B_2$.

The crystals of C-14482 $B_1$ (recrystallized from acetone-hexane) as well as C-14482 $B_2$ and $B_3$, as obtained in Examples 1 through 4 to be described below, show the following properties.

(a) C-14482 $B_1$ (I) Elemental analysis (%) (recrystallized from acetone-hexane and dried under reduced pressure at a room temperature for 30 hours or more):
C, 55.61±1.0
H, 6.31±0.5
N, 13.64±1.0

(II) Melting point: Not lower than 300° C.

(III) Specific rotation:
Unmeasurable (in ethanol).

(IV) Absorption spectra in the ultraviolet and visible regions:
The ultraviolet and visible absorption spectra as measured in methanol are shown in FIG. 1.
$\lambda_{max}^{MeOH}$ 213±3 nm ($E_{1\ cm}^{1\%}$ 592±60)
$\lambda_{max}^{MeOH}$ 283±3 nm ($E_{1\ cm}^{1\%}$ 227±25)
$\lambda_{max}^{MeOH}$ 496±3 nm ($E_{1\ cm}^{1\%}$ 50.1±10)

Figure 2:
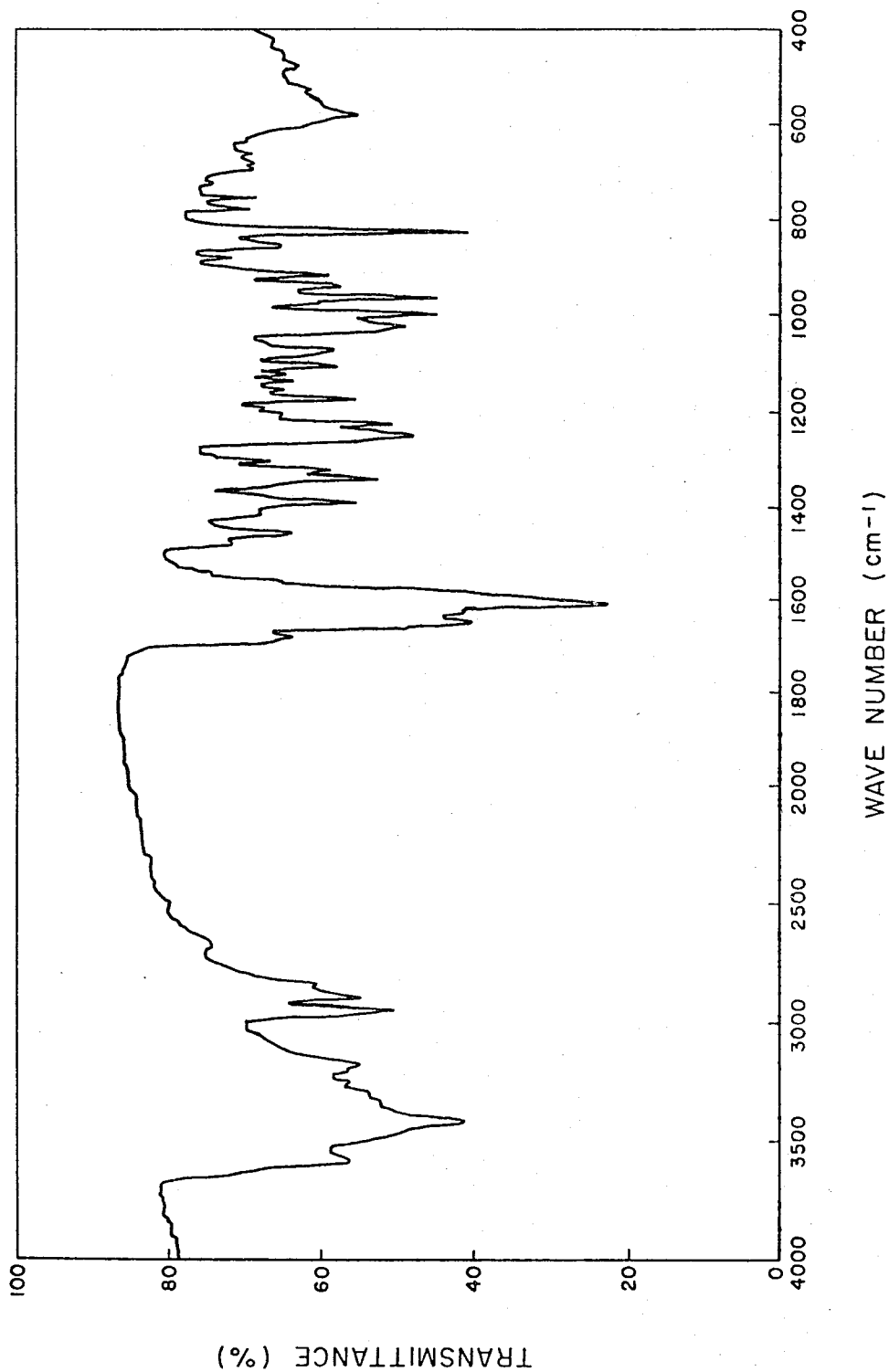

(V) Infrared absorption spectrum
The infrared absorption spectrum as measured by the potassium bromide disc method is shown in FIG. 2. The principal peaks (wave-numbers) are as follows: 3580, 3420, 3175, 2950, 2900, 2840, 1685, 1650, 1610, 1455, 1395, 1345, 1330, 1250, 1230, 1175, 1110, 1075, 1025, 1000, 965, 940, 915, 855, 825, 780, 760 cm$^{-1}$.

(VI) Solubility:
Insoluble in: Hexane, petroleum ether
Slightly soluble in: Ethyl acetate, chloroform, methylene chloride, diethyl ether, water.
Soluble in: Ethanol
Readily soluble in: Methanol, dimethyl sulfoxide.

(VII) Color reactions:
Negative to: Ninhydrin reaction, Sakaguchi reaction
Positive to: Dragendorff's reaction, Barton reaction (gradually turns blue). Potassium permanganate reagent is decolorized.

(VIII) Acidity, neutrality or basicity: Weakly basic (IX) Color:
Dark red to reddish brown (X) Stability:
When heated at 80° C. for 1 hour:
At pH 3, 4 and 5, slightly unstable;
at pH 6, fairly unstable; at pH 7 and 8, unstable.

(XI) Thin-layer chromatography: silica gel (Spot Film f, Tokyo Kasei Co., Japan):
(1) Chloroform-methanol (9:1), Rf 0.37
(2) Ethyl acetate-methanol (1:1), Rf 0.31.

(XII) Formation of salts:
Being a weakly basic substance, C-14482 $B_1$ forms water-soluble salts with inorganic acids, such as hydrochloric acid, sulfuric acid and phosphoric acid, and organic acids, such as formic acid, acetic acid, succinic acid, malonic acid, tartaric acid, citric acid, maleic acid, glucuronic acid, ascorbic acid, lactobionic acid, glucoheptonic acid, glutamic acid, aspartic acid, and methane-sulfonic acid. It also forms sparingly water-soluble salts with picric acid, picrolonic acid, stearic acid, etc. These salts can be prepared by adding directly to a free base of C-14482 B an equivalent of acids and also by utilizing ion exchange resins as shown in Example 2. For example, utilizable in producing the salts are salts forms, e.g. Cl form, phosphoric-acid form, acetic-acid form, etc., of anion exchange resins. Alternatively, these salts can be prepared in an organic solvent by passing for example through a column of salt forms, e.g. Cl-form and acetic-acid form, of an anion exchange resin for nonaqueous solution such as Amberlyste A-21 (Rohm & Haas Co., U.S.).

In particular, the water-soluble salts can be used as preparations for injection, being administered intravenously, intramuscularly and subcutaneously, In addition, they are more stable than the base form and more favored for the use as medicines.

(b) C-14482 B₂

(I) Elemental analysis (%) (dried under reduced pressure at a room temperature for 30 hours or more):
C, $57.40 \pm 1.0$
H, $6.51 \pm 0.5$
N, $13.44 \pm 1.0$ (II) Melting point: Not lower than 300° C.

(III) Absorption spectra in the ultraviolet and visible regions:
$\lambda_{max}^{MeOH}$ 214.5 ± 3 nm ($E_{1\ cm}^{1\%}$ 555 ± 60)
$\lambda_{max}^{MeOH}$ 283 ± 3 nm ($E_{1\ cm}^{1\%}$ 207 ± 25)
$\lambda_{max}^{MeOH}$ 499 ± 3 nm ($E_{1\ cm}^{1\%}$ 55.8 ± 10)

Figure 3:
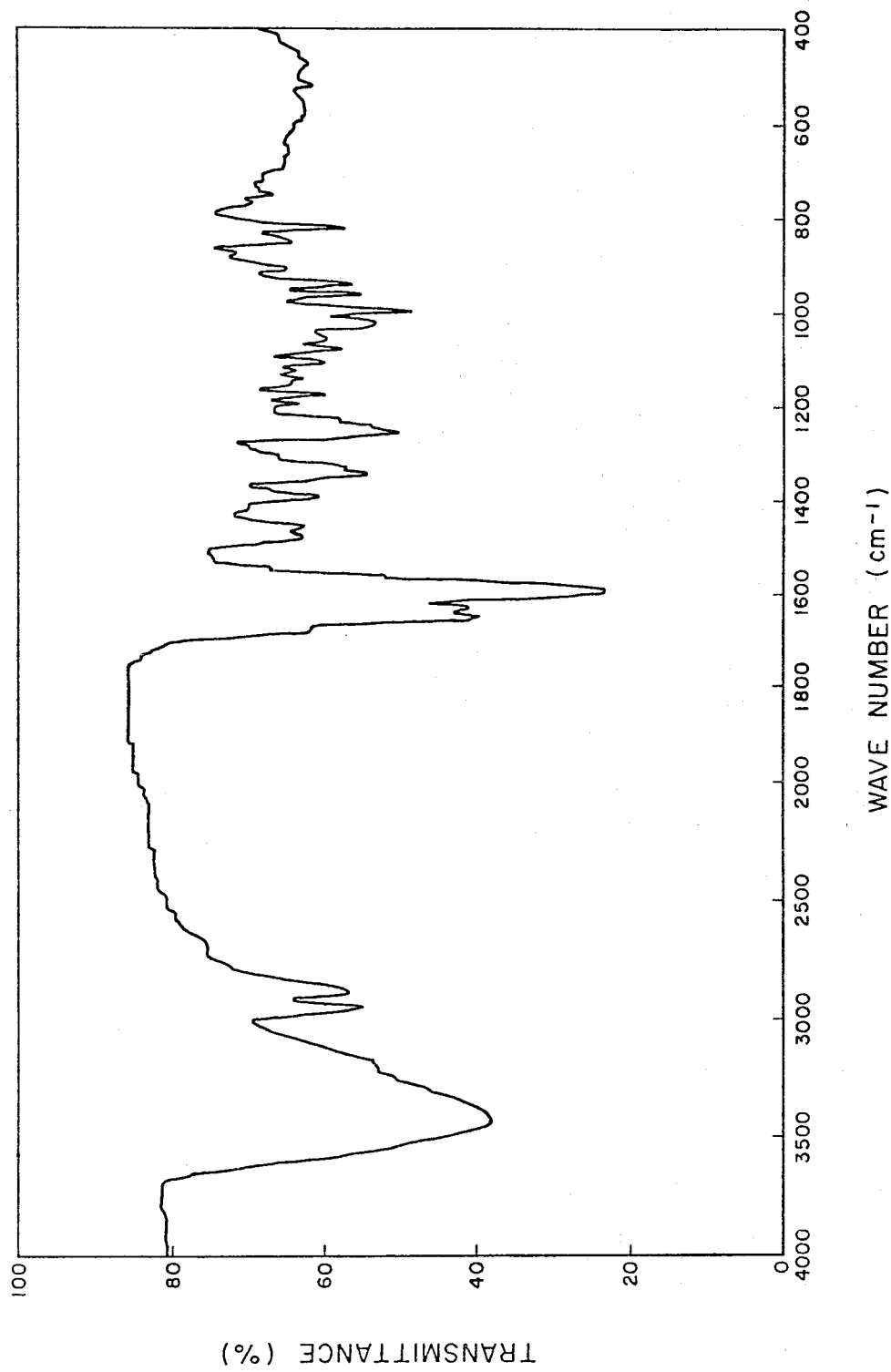

(IV) Infrared absorption spectrum (KBr disc method) (FIG. 3), principal peaks (cm⁻¹): 3430, 2940, 2890, 1680, 1650, 1625, 1590, 1480, 1450, 1390, 1340, 1250, 1175, 1110, 1075, 1055, 1025, 995, 960, 905, 855, 825.

(V) Solubility:
Insoluble in: Hexane, petroleum ether
Slightly soluble in: Ethyl acetate, diethyl ether, water.
Soluble in: Ethanol, chloroform
Readily soluble in: Methanol, dimethylsulfoxide (VI) Color reactions:
Negative to: Ninhydrin reaction, Sakaguchi reaction
Positive to: Dragendorff's reaction, Barton reaction (gradually turns blue); potassium permanganate reagent is decolorized.

(VII) Acidity, neutrality or basicity:
Weakly basic (VIII) Color:
Dark red to reddish brown (IX) Thin-layer chromatography; silica gel (Spot Film f, Tokyo Kasei Co., Japan):
(1) Chloroform-methanol (9:1), Rf 0.43
(2) Ethyl acetate-methanol (1:1), Rf 0.23

(X) Formation of salts:
C-14482 B₂ forms salts with the same inorganic and organic acids as being reacted with C-14482 B₁.

(c) C-14482 B₃

(I) Elemental analysis (%) (dried under reduced pressure at a room temperature for 30 hours or more);
C, $58.74 \pm 1.0$
H, $6.64 \pm 0.5$
N, $14.31 \pm 1.0$ (II) Melting point: Not lower than 300° C.

(III) Absorption spectra in the ultraviolet and visible regions:
$\lambda_{max}^{MeOH}$ 214 ± 3 nm ($E_{1\ cm}^{1\%}$ 620 ± 60)
$\lambda_{max}^{MeOH}$ 283 ± 3 nm ($E_{1\ cm}^{1\%}$ 251 ± 25)
$\lambda_{max}^{MeOH}$ 492 ± 3 nm ($E_{1\ cm}^{1\%}$ 55.6 ± 10)

Figure 4:
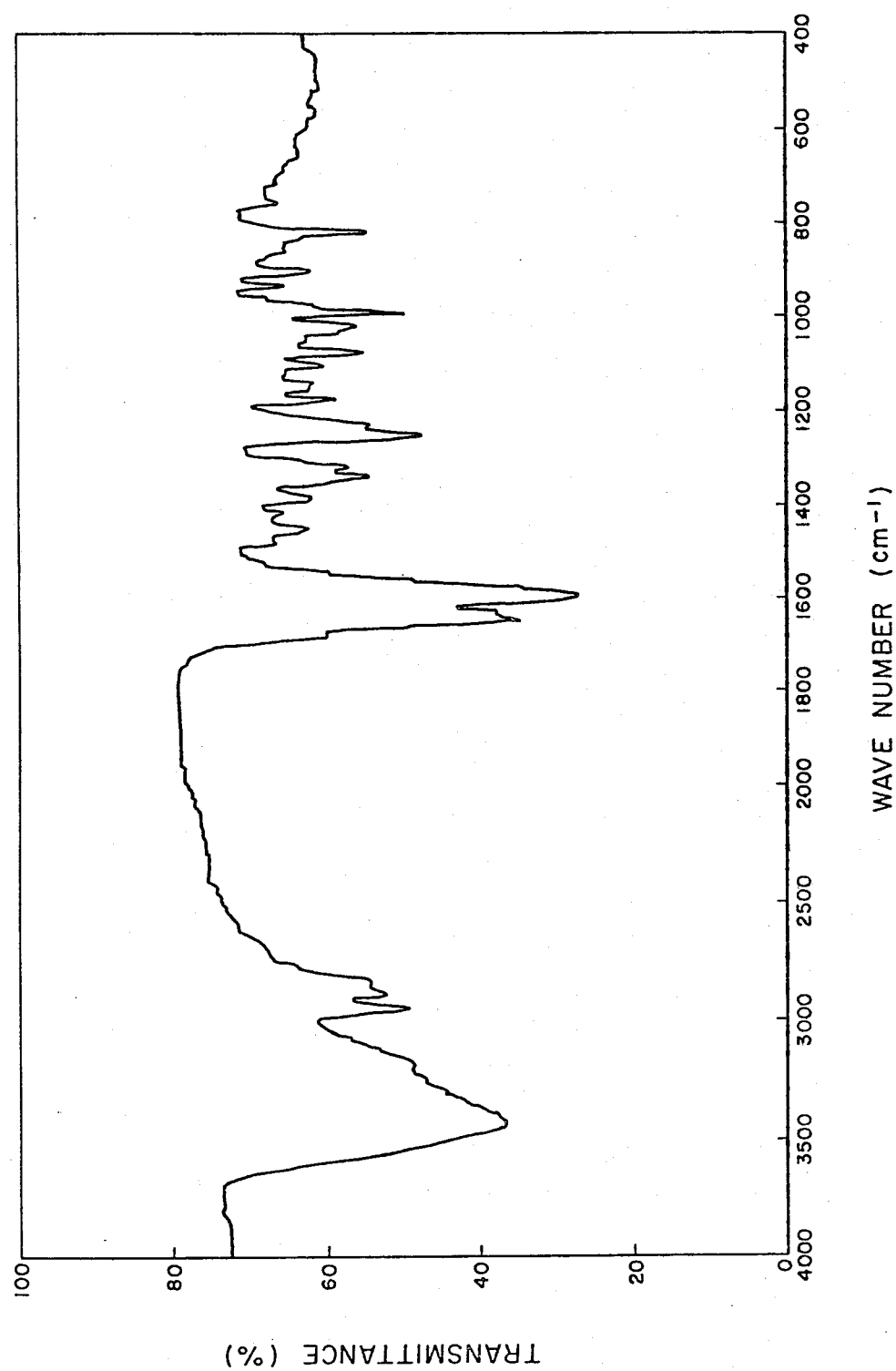

(IV) Infrared absorption spectrum (KBr disc method) (FIG. 4), principal peaks (cm⁻¹): 3430, 2940, 2890, 1680, 1650, 1630, 1595, 1450, 1390, 1340, 1320, 1250, 1175, 1105, 1075, 1020, 995, 935, 905, 825.

(V) Solubility:
Insoluble in: Hexane, petroleum ether
Slightly soluble in: Ethyl acetate, diethyl ether, water.
Soluble in: Ethanol, chloroform
Readily soluble in: Methanol, dimethylsulfoxide (VI) Color reactions:
Negative to: Ninhydrin reaction, Sakaguchi reaction
Positive to: Dragendorff's reaction, Barton reaction (gradually turns blue); potassium permanganate reagent is decolorized.

(VII) Acidity, neutrality or basicity:
Weakly basic (VIII) Color:
Dark red to reddish brown (IX) Thin-layer chromatography; silica gel (Spot Film f, Tokyo Kasei Co., Japan):
(1) Chloroform-methanol (9:1), Rf 0.20
(2) Ethyl acetate-methanol (1:1), Rf 0.18

(X) Formation of salts:
C-14482 B₃ forms salts with the same inorganic and organic acids as being reacted with C-14482 B₁.

Below shown are the biological activities of Antibiotic 14482 B as obtained in Examples 1 through 4.

TABLE 5

Antimicrobial spectrum of Antibiotic C-14482 B₁

| Test organism | Medium | MIC µg/ml |
|---|---|---|
| Escherichia coli K12 IFO 3301 | TSA | 0.2 |
| Escherichia coli NIHJ JC2 | TSA | 0.2 |
| Proteus vulgaris IFO 3045 | TSA | 2 |
| Proteus morganii IFO 3168 | TSA | 2 |
| Proteus mirabilis IFO 3849 | TSA | 0.5 |
| Pseudomonas aeruginosa IFO 3080 | TSA | 0.2 |
| Salmonella typhimurium IFO 12529 | TSA | 0.2 |
| Salmonella enteritidis IFO 3313 | TSA | 0.5 |
| Alcaligenes faecalis IFO 13111 | TSA | 0.05 |
| Enterobacter cloacae IFO 12009 | TSA | 0.2 |
| Serratia marcescens IFO 3046 | TSA | 0.5 |
| Bacillus pumilus IFO 3813 | TSA | 0.2 |
| Bacillus subtilis PCI 219 IFO 3513 | TSA | 0.05 |
| Bacillus cereus IFO 3514 | TSA | 0.2 |
| Bacillus megaterium IFO 12108 | TSA | 0.05 |
| Bacillus brevis IFO 3331 | TSA | 0.1 |
| Staphylococcus aureus FDA 209P IFO 12732 | TSA | 0.01 |
| Micrococcus luteus IFO 12708 | TSA | 0.2 |
| Mycobacterium avium IFO 3143 | TSA . Gly | 0.5 |
| Mycobacterium vaccae ATCC 15483 | TSA . Gly | 1 |
| Mycobacterium smegmatis ATCC 607 | TSA . Gly | 50 |
| Aspergillus niger IFO 4066 | TSA . Glu | 100 |
| Penicillium chrysogenum IFO 4626 | TSA . Glu | 50 |
| Trichophyton rubrum IFO 5467 | TSA . Glu | 50 |
| Saccharomyces cerevisiae IFO 0209 | TSA . Glu | >100 |
| Candida albicans IFO 0583 | TSA . Glu | >100 |

TSA: Trypticase soy agar
TSA . Gly: Trypticase soy agar supplemented with 3% glycerol
TSA . Glu: Trypticase soy agar supplemented with 3% glucose

TABLE 6

Growth inhibition activity against microorganisms

| | Inhibition zone, mm | | |
|---|---|---|---|
| | C-14482 B₁ | C-14482 B₂ | C-14482 B₃ |
| Escherichia coli K-12 IFO 3301 | 22.5 | 20.5 | 0 |
| Proteus mirabilis IFO 3849 | 18.0 | 14.5 | 0 |
| Proteus vulgaris IFO 3045 | 19.5 | 16.5 | 0 |
| Pseudomonas aeruginosa IFO 3080 | 25.5 | 22.5 | 0 |
| Salmonella typhimurium IFO 12529 | 24.0 | 21.5 | 10 |
| Staphylococcus aureus FDA 209P IFO 12732 | 32.5 | 30.5 | 20.5 |
| Bacillus subtilis PCI 219 IFO 3513 | 28.5 | 26.0 | 16.0 |

The growth inhibition activity against microorganisms as described above has been assayed by the paper disc method with the use as the assay medium of Antibiotic Medium 3 (Difco Co., U.S.) containing 1.2% agar. The medicine preparations were used in the form of a methanol solution with the concentration of 20 µg/ml.

In an acute toxicity test with mice (CF #1, male 4-weeks old), a solution of C-14482 B₁ in physiological saline was intravenously administered, and the estimated $LD_{50}$ of the antibiotic was about 0.625 to 1.25 mg/kg.

As described above, Antibiotic C-14482 B according to the present invention exhibits the strong inhibitory activity against gram-negative, gram-positive and acid-fast bacteria, and is therefore useful as antibacterial agents against the bacteria shown in Tables 5 and 6. Furthermore, this substance, with its usefulness as an agent for eliminating R plasmids as well as its possibility of serving as a strong nucleic acid synthesis inhibitor, is expected to be useful as an antitumor agent.

Antibiotic C-14482 B can be used as germicides, disinfectants or drugs for external application, for example, in the disinfection of kitchen wares, surgical instruments, bird cages, human hands, etc. The antibiotic, when it is used as a bactericide or a disinfectant against the bacteria as shown in Tables 5 and 6, may be dissolved in water of 1000 to 2000 ml per 1 mg of the antibiotic to produce a liquid preparation, into which objects are to be soaked for about 10 minutes. To use this antibiotic as a drug for external application, for example, 0.05 mg of Antibiotic C-14482 B can be uniformly admixed with 10 g of white petrolatum to use as an ointment.

Referring to the specific application methods, the antibiotic is utilized as a drug for topical, external application uses by admixing 0.05 mg of C-14482 B with 10 g of white petrolatum and applying the resultant ointment for the purpose of treatment of suppuration caused by *Staphylococcus aureus*; in addition, the above ointment is applied 4 times daily in the amount of about 0.02 to 0.2 g for the treatment of suppuration caused on human hands by the microorganisms as shown in aforementioned Tables 5 and 6.

Antibiotics C-14482 $B_1$, $B_2$ and $B_3$ possess their specific, physicochemical and biological properties, and any corresponding substance having the similar properties is not found among the known metabolites and antibiotics produced by actinomycetes belonging to the genera Streptomyces, Nocardia, Micromonospora, etc., bacteria, fungi and the like, except Antibiotic C-14482 $A_1$ that, as having been described in Japanese Patent Laying-open No. 27501/1979 bears a marked resemblance to the above antibiotics in terms of certain properties such as the absorption spectra in the ultraviolet and visible regions and biological properties. Nevertheless, since the difference from Antibiotic C-14482 $A_1$ is clearly detected in other properties such as the Rf value of the thin layer chromatography, elemental analysis and infrared absorption spectrum, C-14482 $B_1$, $B_2$ and $B_3$ are considered to be the novel antibiotics.

The present invention is to be illustrated in more detail by describing below the Examples, wherein the percent (%), unless otherwise specified, is in weight-/volume percent (w/v %).

The adsorbents used in the present Examples are all the products manufactured by the following companies and shown by the respective trade names as follows:
Rohm & Haas Co., United States:
Amberlite XAD-2 (non-ionic absorption resin)
Amberlite IRC-50 (cation exchange resin)
Amberlyste A-21 (anion exchange resin for non aqueous solvent)
Mitsubishi Chemical Industries, Ltd., Japan;
Diaion HP-10 (non-ionic absorption resin)
Pharmacia Co., Sweden: Sephadex LH-20 (dextran gel)
E. Merck A. G. of Fedral Republic of Germany; $HF_{254}$ (sillica gel for thin-layer chromatography)

EXAMPLE 1

A culture of the strain Nocardia sp. No. C-14482 IFO 13887 (ATCC 31487, IFO 13887), the Antibiotic C-14482 B producing microorganism, on a yeast extract-malt extractagar slant was used to inoculate a 200 ml conical flask containing 40 ml of a seed culture medium (pH 7.0) composed of 2% of glucose, 3% of soluble starch, 1% of soybean flour, 1% of corn steep liquor, 0.5% of polypeptone, 0.3% of NaCl, and 0.5% of $CaCO_3$, and shake culture was carried out on a rotary shaker at 28° C. for 48 hours, whereby a seed culture was obtained. A 0.5 ml portion of this seed culture is transferred to a conical flask of 200 ml capacity containing 40 ml of a fermentation medium (pH 7.0) composed of 5% of dextrin, 3% of corn steep liquor, 0.1% of polypeptone, 1% of $CaCl_2$, and 0.5% of $CaCO_3$, which was then incubated on a rotary shaker at 28° C. for 66 hours. The resulting broth was assayed by an agar dilution method against *Escherichia coli* K-12 IFO 3301 and *Proteus mirabilis* IFO 3849 as test organisms using C-14482 $B_1$ as the standard. The titer thus found was 10 $\mu$g/ml.

EXAMPLE 2

A 10 ml portion of the seed culture obtained in Example 1 was transferred to a Sakaguchi flask of 2-liter capacity containing 500 ml of a seed culture medium, and the inoculated medium was cultivated on a reciprocating shaker at 28° C. for 48 hours. One liter of the culture was used to inoculate a 200-liter stainless steel tank containing 100 l of the seed culture medium, and incubation was carried out at 28° C. for 48 hours, with aeration at the rate of 100 l/min. and agitation at 200 r.p.m. to obtain a seed culture. This seed culture was transferred to a 2000-liter stainless steel tank containing 1000 l of a fermentation medium as shown in Example 1. The inoculum size used was 10% and incubation was carried out at 28° C. for 90 hours, with aeration at the rate of 1000 l/min., agitation at 150 r.p.m. ($\frac{4}{3}$ DT) and an internal pressure of 1 kg/cm². The resultant culture broth showed a titer of 5 $\mu$g/ml as assayed in the same manner as described in Example 1.

EXAMPLE 3

The culture broth in the volume of 1160 l as obtained in Example 2 was adjusted to pH 5.0 with dilute aqueous sulfuric acid and filtered after addition of 35 kg of Hyflo-Supercel (Johnes Manville Co., United States) 1180 l of the resultant filtrate was adjusted to pH 6.0 and passed through a column of 100 l of Diaion HP-10. The column was washed with 300 l of water, followed by elution with 400 l of 80 v/v % aqueous methanol.

The eluate, after being adjusted to pH 4.5, was concentrated under reduced pressure to distill off methanol, and 60 l of the concentrate was adjusted to pH 8.0 and then extracted with 20 l portion each of isobutanol three times. The extracts of the isobutanol layers were pooled and shaken with 35 l portion each of N/200 hydrochloric acid twice. The aqueous layers were pooled, adjusted to pH 6.0 and concentrated under reduced pressure to distill off isobutanol. 40 l of the residual aqueous solution was brought to pH 6.0 and was adsorbed on a 25-liter column of Diaion HP-10.

After washing the column with 75 l of water, elution was carried out with 100 l of 80 v/v % aqueous methanol. The eluate was adjusted to pH 4.5 and concentrated under reduced pressure. 2 l of the resultant concentrate was adjusted to pH 8.0 and extracted with 0.7 l portion each of chloroform five times. The extracts were pooled, concentrated under reduced pressure to 1 l, and the active substances were transferred twice with 0.5 l of N/50 hydrochloric acid into an aqueous layer. 1 l of the aqueous hydrochloric acid layer was brought to pH 8.0, and extracted again with 0.5 l of chloroform five times, followed by drying the chloroform layer with anhydrous sodium sulfate and concentrating under reduced pressure at low temperature. By the above procedure, there was obtained 7.7 g of a crude product (I).

7.7 g. of the crude product is dissolved in 13 ml of methanol, followed by admixing with 80 ml of 0.1 N hydrochloric acid and 160 ml of water and carrying out filtration. The filtrate, after adding water, was adjusted to pH 6.0, and passed through a 500 ml column of Amberlite XAD-2. The column was developed with 1.5 l of 5% aqueous methanol, and 700 ml of the active fraction being initially eluted was adjusted to pH 8.0 and then extracted with 300 ml portion each of chloroform five times. The extracts were dried over anhydrous sodium sulfate, and concentrated under reduced pressure, whereby the deposited crystalline substance was recovered by filtration and dried, resulting in 849 mg of crude crystals of C-14482 $B_1$. Recrystallization of 700 mg of the crude C-14482 $B_1$ from acetone-n-hexane yields 360 mg of purified crystals of C-14482 $B_1$. In addition, there was recovered 60 mg of crystals of C-14482 $B_1$ from the resultant mother liquor.

From the mother liquor in the case of recovery of crude crystals of C-14482 $B_1$ as above mentioned, there was obtained 1.6 g of a mixture containing active substances such as C-14482 $B_1$, $B_2$ and $B_3$.

On the other hand, the concentrate (60 l) of the active fraction (400 l) eluted from the first Diaion HP-10 column was extracted with isobutanol and the residual water layer further concentrated to distill off isobutanol, and passed through a 10 l column of Amberlite IRC-50 (H-type), followed by washing with water and eluting with 120 l of 0.2 N hydrochloric acid.

The eluate was adjusted to pH 6.0 and was adsorbed on a 25 l column of Diaion HP-10, followed by washing with 75 l of water and eluting with 100 l of 80 v/v % aqueous MeOH. The eluate was adjusted to pH 4.5 and concentrated under reduced pressure to 1.6 . The concentrate was brought to pH 8.0, and extracted with 0.8 l of chloroform five times. The extracts were combined, dried over anhydrous sodium sulfate and concentrated under reduced pressure, resulting in 2.5 g of a crude product (II) containing C-14482 $B_1$.

Also from the said crude product (II), by purifying with a column of Amberlite XAD-2 as described above, there were obtained crystals of C-14482 $B_1$ and a mixture containing C-14482 $B_1$, $B_2$ and $B_3$.

Then, referring to C-14482 $B_2$, the mother liquor in the case of recovery of the purified C-14482 $B_1$ crystals obtained from the above-mentioned crude product (I) was concentrated to dryness, and the residue was extracted with a small amount of chloroform, whereby the soluble portion was again concentrated to dryness. The resultant mixture containing C-14482 $B_1$ and $B_2$ was chromatographed on thin-layer silica gel ($HF_{254}$) at low temperature (solvent system; ethyl acetate: methanol=3:2), and the band of silica gel corresponding to C-14482 $B_2$ was scraped off to be extracted with ethanol. The extract was concentrated, and chromatographed on a column of Sephadex LH-20 at a temperature of not higher than 10° C., followed by carrying out elution with ethanol. The fractions corresponding to C-14482 $B_2$ were pooled and concentrated, thus resulting in 10 mg of a purified product of C-14482 $B_2$.

Also, 1.6 g of the mother liquor portion in relation to the crude crystals of C-14482 $B_1$ was repeatedly chromatographed on thin-layer silica gel ($HF_{254}$) with chloroform: methanol (9:1) and ethyl acetate: methanol (3:2), followed by subjecting to column chromatography on Sephadex LH-20. By the above procedure were obtained 10 mg and 4 mg of the purified C-14482 $B_2$ and $B_3$ products, respectively.

EXAMPLE 4

In 2 ml of methanol was dissolved 40 mg of crystals of C-14482 $B_1$ as obtained in Example 3, and the solution was passed through a 6.5 ml column of Amberlyste A-21 (Cl form). The red-colored active fractions were pooled, concentrated and replaced with water to effect lyophilization, whereby there was obtained 39 mg of a hydrochloride of C-14482 $B_1$ was powder.

The ultraviolet absorption spectrum: $\lambda_{max}^{MeOH}$ 214 nm ($E_{1cm}^{1\%}$ 507), 281 nm ($E_{1cm}^{1\%}$ 187), 497 nm ($E_{1cm}^{1\%}$ 43.2).

Elemental analysis (dried at a room temperature) (found): C, 50.27, 50.63; H, 6.14, 6.27; N, 12.06, 11.49; Cl, 7.07, 7.26.

EXAMPLE 5

A culture of the strain Nocardia sp. No. C-14482 IFO 13725 (ATCC 31309, IFO 13725), the Antibiotic C-14482 B. producing microorganism, on a yeast extract-malt extract-agar slant was incubated in the same manner as described in Example 1. The culture broth thus obtained, when being assayed by the same procedure as in Example 1, showed the titer of 0.5 μg/ml as the mixture of C-14482 $B_1$, $B_2$ and $B_3$.

What we claim is:

1. Antibiotics C-14482 $B_1$, $B_2$ or $B_3$ which have the following properties, and their salts
   (a) Antibiotic C-14482 $B_1$:
   (1) Elemental analysis (%) (recrystallized from acetone-hexane and dried under reduced pressure at a room temperature for 30 hours or more):
   C 55.61±1.0
   H 6.31±0.5
   N 13.64±1.0
   (2) Melting point: Not lower than 300° C.
   (3) Absorption spectra in the ultraviolet and visible regions:
   $\lambda_{max}^{MeOH}$ 213±3 nm ($E_{1cm}^{1\%}$ 592±60)
   $\lambda_{max}^{MeOH}$ 283±3 nm ($E_{1cm}^{1\%}$ 227±25)
   $\lambda_{max}^{MeOH}$ 496±3 nm ($E_{1cm}^{1\%}$ 50.1±10)
   (4) Infrared absorption spectrum (KBr disc method), principal peaks ($cm^{-1}$): 3580, 3420, 3175, 2950, 2900, 2840, 1685, 1650, 1610, 1455, 1395, 1345, 1330, 1250, 1230, 1175, 1110, 1075, 1025, 1000, 965, 940, 915, 855, 825, 780, 760;
   (5) Solubility:
   Insoluble in: Hexane, petroleum ether
   Slightly soluble in: Ethyl acetate, chloroform, methylene chloride, diethyl ether, water;
   Soluble in: Ethanol
   Readily soluble in: Methanol, dimethyl sulfoxide
   (6) Color reactions:
   Negative to: Ninhydrin reaction, Sakaguchi reaction;

Positive to: Dragendorff's reaction, Barton reaction; Potassium permanganate reagent is decolorized;
(7) Acidity, neutrality of basicity: Weakly basic
(8) Color: Dark red or reddish brown
(9) Thin-layer chromatography; silica gel (Spot film f, Tokyo Kasei Co., Japan)
  (i) Chloroform-methanol (9:1), Rf 0.37
  (ii) Ethyl acetate-methanol (1:1), Rf 0.31
(b) Antibiotic C-14482 $B_2$:
(1) Elemental analysis (%) (dried under reduced pressure at a room temperature for 30 hours or more):
  C $57.40 \pm 1.0$
  H $6.51 \pm 0.5$
  N $13.44 \pm 1.0$
(2) Melting point: Not lower than 300° C.
(3) Absorption spectra in the ultraviolet and visible regions:
  $\lambda_{max}^{MeOH}$ $214.5 \pm 3$ nm ($E_{1cm}^{1\%}$ $555 \pm 60$)
  $\lambda_{max}^{MeOH}$ $283 \pm 3$ nm ($E_{1cm}^{1\%}$ $207 \pm 25$)
  $\lambda_{max}^{MeOH}$ $499 \pm 3$ nm ($E_{1cm}^{1\%}$ $55.8 \pm 10$)
(4) Infrared absorption spectrum (KBr disc method), principal peaks (cm$^{-1}$): 3430, 2940, 2980, 1680, 1650, 1625, 1590, 1480, 1450, 1390, 1340, 1250, 1175, 1110, 1075, 1055, 1025, 995, 960, 940, 905, 855, 825;
(5) Solubility:
  Insoluble in: Hexane, petroleum ether
  Slightly soluble in: Ethyl acetate, diethyl ether, water
  Soluble in: Ethanol, chloroform
  Readily soluble in: Methanol, dimethyl sulfoxide
(6) Color reaction:
  Negative to: Ninhydrin reaction, Sakaguchi reaction;
  Positive to: Dragendorff's reaction, Barton reaction; Potassium permanganate reagent is decolorized;
(7) Acidity, neutrality or basicity: Weakly basic
(8) Color: Dark red or reddish brown
(9) Thin-layer chromatography; silica gel (spot film f. Tokyo Kasei Co., Japan)
  (i) Chloroform-methanol (9:1), Rf 0.43
  (ii) Ethyl acetate-methanol (1:1), Rf 0.23
(c) Antibiotic C-14482 $B_3$:
(1) Elemental analysis (%) (dried under reduced pressure at a room temperature for 30 hours or more):
  C $58.74 \pm 1.0$
  H $6.64 \pm 0.5$
  N $14.31 \pm 1.0$
(2) Melting point: Not lower than 300° C.
(3) Absorption spectra in the ultraviolet and visible regions:
  $\lambda_{max}^{MeOH}$ $214 \pm 3$ nm ($E_{1cm}^{1\%}$ $620 \pm 60$)
  $\lambda_{max}^{MeOH}$ $283 \pm 3$ nm ($E_{1cm}^{1\%}$ $251 \pm 25$)
  $\lambda_{max}^{MeOH}$ $492 \pm 3$ nm ($E_{1cm}^{1\%}$ $55.6 \pm 10$)
(4) Infrared absorption spectrum (KBr disc method), principal peaks (cm$^{-1}$): 3430, 2940, 2890, 1680, 1650, 1630, 1595, 1450, 1390, 1340, 1320, 1250, 1175, 1105, 1075, 1020, 995, 935, 905, 825;
(5) Solubility:
  Insoluble in: Hexane, petroleum ether
  Slightly soluble in: Ethyl acetate, diethyl ether, water
  Soluble in: Ethanol, chloroform
  Readily soluble in: Methanol, dimethyl sulfoxide
(6) Color reaction:
  Negative to: Ninhydrin reaction, Sakaguchi reaction
  Positive to: Dragendorff's reaction, Barton reaction; Potassium permanganate reagent is decolorized;
(7) Acidity, neutrality or basicity: Weakly basic
(8) Color: Dark red or reddish brown
(9) Thin-layer chromatography; silica gel (Spot Film f, Tokyo Kasei Co., Japan)
  (i) Chloroform-methanol (9:1), Rf 0.20
  (ii) Ethyl acetate-methanol (1:1), Rf 0.18.

2. A method for producing Antibiotics C-14482 $B_1$, $B_2$ and/or $B_3$ characterized by cultivating a microorganism which belongs to the genus Nocardia and is capable of producing Antibiotics C-14482 $B_1$, $B_2$ and/or $B_3$ in a culture medium therefor to produce and accumulate Antibiotics C-14482 $B_1$, $B_2$ and/or $B_3$ in the culture broth and extracting the antibiotics therefrom.

3. A method as claimed in claim 2, wherein the microorganism is Nocardia sp. No. C-14482 (ATCC 31309).

4. A method as claimed in claim 2, wherein the microorganism is Nocardia sp. No. C-14482 (ATCC 31487).

5. A pure culture of the microorganism belonging to the genus Nocardia having the characteristics identifiable with those of ATCC 31487,
said culture being capable of producing in a culture medium containing assimilable carbon and digestible nitrogen sources, a recoverable amount of Antibiotics C-14482 $B_1$, $B_2$ and/or $B_3$.

* * * * *